United States Patent
Schwarz

(10) Patent No.: US 7,460,218 B2
(45) Date of Patent: Dec. 2, 2008

(54) DEVICE AND METHOD FOR DETERMINING THE PROPERTIES OF SURFACES

(75) Inventor: Peter Schwarz, Königsdorf (DE)

(73) Assignee: BYK Gardner GmbH, Geretsried (DE)

( * ) Notice: Subject to any disclaimer, the term of this patent is extended or adjusted under 35 U.S.C. 154(b) by 512 days.

(21) Appl. No.: 10/824,066

(22) Filed: Apr. 14, 2004

(65) Prior Publication Data

US 2004/0239919 A1      Dec. 2, 2004

(30) Foreign Application Priority Data

Apr. 30, 2003      (DE) ................................. 103 19 543

(51) Int. Cl.
*G01N 21/00*      (2006.01)
(52) U.S. Cl. .................. 356/237.2; 356/237.4
(58) Field of Classification Search ........................ None
See application file for complete search history.

(56) References Cited

U.S. PATENT DOCUMENTS

| | | | | |
|---|---|---|---|---|
| 4,768,878 A | * | 9/1988 | Heine et al. ............... 356/237.2 |
| 4,933,567 A | * | 6/1990 | Silva et al. ................... 356/430 |
| 6,509,964 B2 | * | 1/2003 | Wiles et al. ............... 356/237.2 |
| 6,542,248 B1 | * | 4/2003 | Schwarz ..................... 356/600 |
| 6,654,132 B1 | * | 11/2003 | Schietinger et al. ......... 356/630 |
| 6,822,734 B1 | * | 11/2004 | Eidelman et al. ......... 356/237.2 |
| 6,842,250 B2 | * | 1/2005 | Schwarz ..................... 356/445 |

FOREIGN PATENT DOCUMENTS

DE      4319869 A1  *  12/1994

* cited by examiner

*Primary Examiner*—Michael A. Lyons
*Assistant Examiner*—Juan D Valentin
(74) *Attorney, Agent, or Firm*—Greer, Burns & Crain, Ltd.

(57) ABSTRACT

The present invention relates to a device and a method for determining the properties of surfaces having at least one first radiation means for collimated irradiation of a measurement surface to be examined and at least one second radiation means for non-collimated irradiation of said measurement surface wherein the space above said measurement surface has substantially radiation-absorbing properties.

The device of the invention further comprises at least one radiation detector means which captures at least a portion of the radiation reflected and/or diffused off the surface to be examined and emits at least one measurement signal which is characteristic of the reflected and/or diffused radiation.

31 Claims, 1 Drawing Sheet

DEVICE AND METHOD FOR DETERMINING THE PROPERTIES OF SURFACES

BACKGROUND OF THE INVENTION

The present invention relates to a device and a method for determining the properties of surfaces.

The quality of visible surfaces is a significant property of objects used in everyday life such as furnishings and consumer items such as cars and the like, thus decisively determining their overall impression on a human observer. An example therefor are high-gloss or metallic finishes of car bodies. The reproducible evaluation of the quality of surfaces in particular of said high-gloss finishes requires measuring instruments which capture precisely those physical quantities which decisively determine the overall impression on a human observer. Various methods and devices are known in the prior art for determining the visual properties and specifically the reflection characteristics of surfaces.

One drawback of these measuring devices is that they use substantially collimated light, i.e. directional parallel light beams for determining the reflection or diffusion characteristics of the object to be examined. On the one hand, such devices are capable of simulating the reflection characteristics for example of finished car body parts on cloudless days because then sunlight may be considered to be substantially collimated light.

However, finished surfaces in particular may also show properties whose overall impression will only become apparent to a human observer on overcast days because then the light will impinge on the surface to be examined from a plurality of directions, being scattered by the clouds i.e. uncollimated or diffused, respectively. Thus the problem is that the impression which the surface actually gives to a human observer results from the kind of illumination, i.e. whether the object is illuminated by collimated and/or uncollimated light or these types interact.

BRIEF SUMMARY OF THE INVENTION

The object of the present invention is therefore to provide a device and a method of the type mentioned initially which allows a reproducible evaluation of the overall impression of surfaces under lighting conditions or kinds of illumination defined in particular but not exclusively with regard to the degree of collimation.

The said device can in particular capture the reflection properties of a surface to be evaluated employing non-collimated, i.e. as a rule scattered or diffused light.

The properties of surfaces or properties of textured surfaces, respectively, in the scope of the present invention are understood to mean those physical properties of a surface which are decisive for the appearance of a surface to a human observer. These include above all properties such as macro- und microtexture, topography, color, color location, color brightness, gloss, distinctness of image (DOI), haze, surface textures and orange peel etc.

The device of the present invention uses a first radiation means having at least one radiation source to direct substantially collimated radiation towards the measurement surface at a predetermined angle. Said predetermined angle is preferably variable.

Moreover, in said device at least one second radiation means having at least one radiation source is provided which emits substantially non-collimated radiation onto the measurement surface.

Further, the device of the invention comprises at least one radiation detector means which captures at least a portion of the radiation reflected and/or diffused off the measurement surface and emits at least one measurement signal which is characteristic of the reflected and/or diffused radiation. The radiation detector means may also comprise a device suitable for detecting incident radiation dependent on its wavelength. For example, a monochromator may be provided or generally at least one dispersive component such as transmission or reflection gratings or the like. Preferably said angle, which is formed by a geometrical connecting axis from the radiation detector means to the geometrical center of the measurement surface and projection of said connecting axis onto the measurement surface, is variable wherein the distance between the radiation detector means and the measurement surface preferably remains substantially constant. The device of the invention is remarkable in that the space above the measurement surface possesses substantially radiation-absorbing properties wherein the radiation captured by and reflected and/or diffused off the radiation detector means is substantially only that radiation diffused and/or reflected off the surface to be examined. Otherwise possible multiple reflection or diffusion would considerably complicate any interpretation of the measurement signals determined by the radiation sensors for characterizing the surface. Besides it should also be prevented that light reflected or diffused off the measurement surface is reflected through the space above the measurement surface and in turn transmitted to the measurement surface as non-collimated light. However, corresponding embodiments which can eliminate the influence of such effects using calculation techniques of the provided processor means are likewise conceivable.

The term "space" in this context may mean both a physical, spatial delimitation of the measurement surface from the surroundings or only those devices of the invention positioned above the measurement surface.

In a preferred embodiment of the device of the invention, the angle formed by a first geometrical connecting axis from at least one radiation detector means to the geometrical center of the measurement surface and projection of said first connecting axis onto the measurement surface, and preferably also that angle formed by a second geometrical connecting axis from a first radiation means to the geometrical center of the measurement surface and projection of said second connecting axis onto the measurement surface, is variable.

In the device of the invention it is preferred to keep the distance between the first radiation means and the measurement surface sufficiently small so as to allow a compact construction so that the device can also be designed for example as a handheld device. Preferably said distance is between 1 cm and 30 cm, preferred between 2 cm and 20 cm, particularly preferred between 2 cm and 7 cm.

In a preferred embodiment of the invention, a plurality of second radiation means is provided to achieve a particularly advantageous, uniform, non-collimated radiation.

In a preferred embodiment of the device of the invention, said at least one second radiation means comprises at least one radiation diffusor means which diffuses radiation from the one or more radiation sources of said second radiation means at least partially in random directions onto the measurement surface.

It is preferred that the diffusing components of the radiation diffusor means are radiation diffusor disks, frosted glass disks, diffusor films and the like.

In order to achieve the diffusor effect, the effective diffusing surface of the radiation diffusor means, i.e. that portion of the radiation diffusor means which receives the radiation from the radiation sources of the second radiation means and diffuses it, is positioned at a specified angle relative a geometrical connecting line between said radiation means and the geometrical center of the measurement surface. Said angle of the diffusor surface is between 0 degrees and 90 degrees, preferred between 30 degrees and 90 degrees, particularly preferred between 75 degrees and 90 degrees.

A preferred embodiment of the device of the invention provides for the spatial orientation and position of the diffusor surfaces of at least one radiation diffusor means to be variable by means of corresponding devices relative the geometrical connecting axis between the radiation diffusor means and the geometrical center of the measurement surface.

In a further advantageous embodiment of the device of the invention, the at least one first and at least one second radiation means are mounted in a housing above the measurement surface. In this way, for example an influence of radiated interference caused by daylight can be prevented.

Preferably the space inside the housing has substantially radiation-absorbing properties.

In a preferred embodiment of the device of the invention the housing is substantially constructed radiation-proof, preferably light-proof such that substantially no radiation can enter the housing other than such as diffused and/or reflected off the measurement surface.

In a further preferred embodiment of the invention, at least the second radiation means are preferably equally distributed on a geometrical spherical surface or on the geometrical surface of a rotational ellipsoid above the measurement surface so as to cause a preferably uniform irradiation of the measurement surface.

In an embodiment of the device of the invention it is preferred to vary at least one radiation source in at least one radiation parameter such as radiation intensity, radiation wavelength, direction of radiation polarization, temporal radiation intensity modulation and the like.

In a further preferred embodiment of the device at least two radiation sources are variable independent of each other in at least one radiation parameter.

Preferably the radiation sources of the device of the invention are selected from a group of radiation sources comprising thermal radiation sources, in particular—but not exclusively—light bulbs, halogen light bulbs, furthermore coherent and non-coherent semiconductor radiation sources, gas discharge radiation sources, lasers and the like.

In a further preferred embodiment of the device of the present invention at least two, preferably three or more radiation sources and/or radiation detector means are configured such that they differ in their spectral characteristics, i.e. their wavelength-specific radiation emission characteristics or response behavior to different wavelengths are different.

In a preferred embodiment of the device of the invention, the radiation of the at least one first radiation means is collimated, i.e. at least one radiation directing means generates a parallel radiation bundle.

The preferred radiation directing means employed, in particular with light being used, can be lens components, micro lens components, micro lens arrays, diffracting components, reflector components, in particular—but not exclusively—concave reflectors, grating components, volume grating components, holographic components and the like.

It is further preferred that diaphragm means, preferably but not exclusively apertured diaphragms, vary the expansion of the collimated radiation bundles of the first radiation means.

Said device is preferably movable relative the measurement surface such that the distance between the radiation means and the measurement surface remains substantially constant wherein the surface properties of various areas of a large measurement surface can be characterized in an advantageous manner by capturing the relevant measurement signals using one single device.

In a further preferred embodiment of the device of the invention at least one travel measurement means is provided which emits at least one measurement signal which is characteristic of the traveled distance of the relative movement from the device of the invention to the measurement surface.

At least one travel measurement means may preferably be positioned inside or outside the housing.

In a further preferred embodiment of the device of the invention at least one coating-thickness measurement means is provided for determining the coating thickness of the surface to be examined comprising at least one coating thickness sensor which emits a measurement signal representative of the coating thickness to be determined wherein said coating thickness sensor is selected from a group of coating thickness sensors comprising, depending on the material of the surface to be examined, magnetic flux density sensors, eddy current sensors, ultrasonic sensors, mechanical thickness sensors and the like.

In this way the surface to be examined can be characterized, in addition to its reflection and diffusion properties, also through measuring the thickness of a coating if any is present.

At least one coating-thickness measurement means may preferably be positioned inside and/or outside a housing.

In a further preferred embodiment the device of the invention comprises at least one processor means and one memory means which allow an allocation of the measurement signals of the radiation detector means and/or the measurement signals of the travel measurement means and/or the coating-thickness measurement means to specified locations, in particular—but not exclusively—to the same location on the measurement surfaces. To this end it is preferred that for example when starting the measuring, e.g. when the device of the invention is placed on the measurement surface, a reference point is specified preferably automatically by a suitable switch and its characteristic coordinates are stored in the memory means.

This will be in particular advantageous when the measurement surface areas to be examined at specified times by different measurement means are physically separate so that if the measurement signals are to be correlated they can be stored temporarily and subsequently allocated to one another and to the matching location on the measurement surface.

The object is further solved through a method for a quantified determination of the properties of surfaces.

The method of the invention is remarkable in that at least one first radiation means and at least one second radiation means projects at least a portion of the radiation from its at least one radiation source onto the measurement surface and at least one provided radiation detector means captures at least a portion of the radiation reflected and/or diffused off the measurement surface and emits at least one measurement signal which is characteristic of the reflected and/or diffused radiation, and that at least one control means is provided for controlling the capture of the measurement signals by the radiation detector means, and that at least one output means is provided for outputting the at least one measurement result.

In a preferred embodiment of the method of the invention at least one processor means is provided for evaluating the measurement signals and deriving therefrom at least one parameter which characterizes the properties of the measurement surface and which can be displayed at least on one output means.

A preferred embodiment of the method of the invention is characterized in that at least one control means is provided for controlling the capture of the measurement signals of the radiation detector means and/or the travel measurement means and/or the coating-thickness measurement means and storing same in at least one provided memory means.

In a preferred embodiment of the method of the invention the radiation from the second radiation means is substantially reflected and/or diffused only once off the measurement surface and/or off a surface substantially parallel thereto.

Further advantages, features and application possibilities of the present invention will now be specified in the following description of embodiments in conjunction with the drawings.

DETAILED DESCRIPTION OF THE INVENTION

Figure 1:
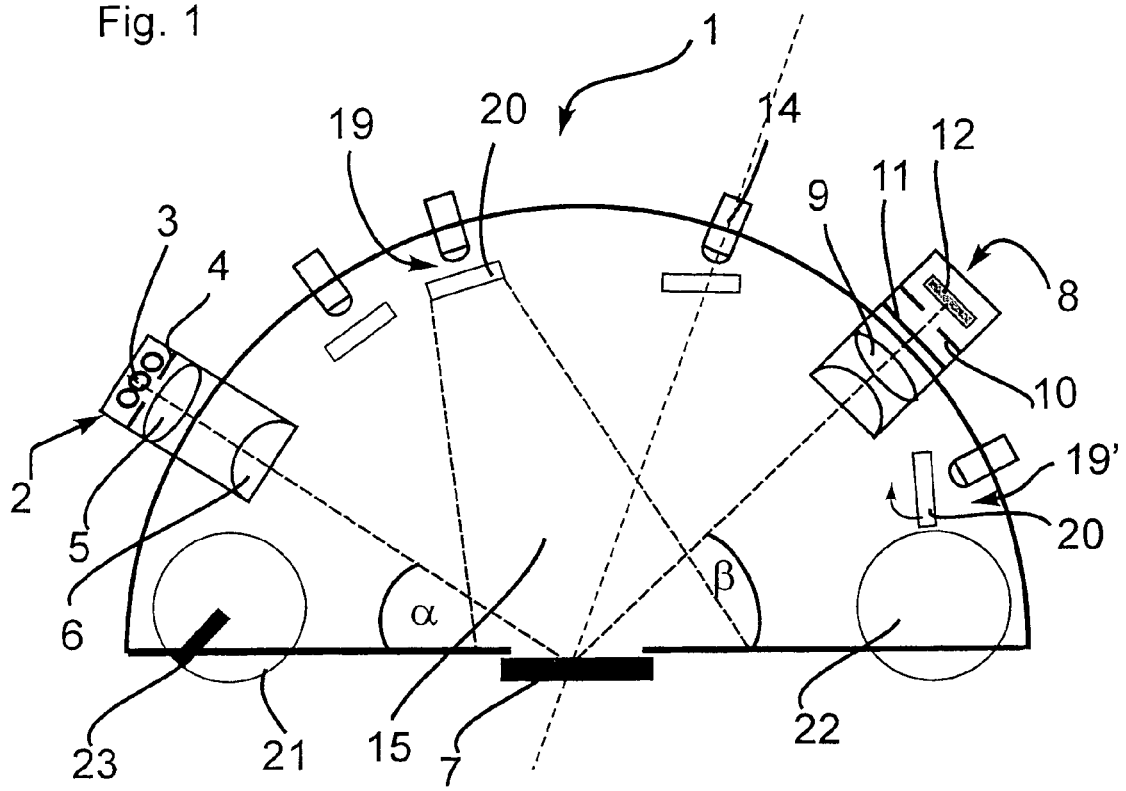
FIG. 1 a schematic illustration of a first embodiment according to the present invention.

The device illustrated schematically in FIG. 1 for determining the properties of surfaces comprises a hemispherical housing 1 in which a first radiation means 2 is positioned at a specified angle a relative to a measurement surface 7.

The radiation in the present embodiment is light visible to the human eye. Corresponding to the device of the invention, utilizing radiation of other wavelengths such as infrared or UV radiation may, however, also be useful and advantageous.

The radiation means 2 includes—indicated schematically—three light sources 3, a diaphragm 4 and a lens means 5. The light emitting from one of the light sources 3 is limited in its aperture 6 by the diaphragm 4 and collimated by the lens means 5, i.e., it is substantially bundled in parallel and impinges on the measurement surface 7 to be examined through the aperture 6.

The measurement surface 7 reflects at least a portion of the light, causing it to enter into a radiation detector means 8 which also comprises a lens 9, a diaphragm 10, a filter 11 and a light sensor 12. The radiation detector means 8 may be positioned at substantially the same angle α as the first radiation means 2 relative the measurement surface 7 but it is preferably positioned at a different angle β.

Further, four second radiation means 19 in the sense of the device of the invention are positioned in the housing 1, such as the second radiation means with a radiation source 14, the light of which is substantially projected onto a diffusor 20 which in turn diffuses it in random directions, i.e. non-collimated, onto the measurement surface 7. The light cone of non-collimated light thus generated is designated with 15.

It is indicated schematically that the second radiation means 19 are positioned in the hemispherical housing 1 in a certain way, preferably such that the measurement surface is irradiated as uniformly as possible with non-collimated light. The radiation means 19 are positioned not only on the plane illustrated in FIG. 1 but also spatially distributed.

The diffusor means in the shape of diffusor 20 is positioned relative a geometrical connecting axis from the second radiation means 19 to the geometrical center of the measurement surface 7 at a predetermined angle which, to achieve an appropriate diffusing effect, is between 0 degrees and 90 degrees but should preferably not be precisely 90 degrees.

A second irradiation source 19' and a corresponding diffusor 20' indicate schematically that said angle is variable. The embodiment illustrated in FIG. 1 is furthermore substantially movable across the measurement surface 7 via illustrated wheels 21 and 22 such that the distance between the radiation means 2 and 19 and the radiation detector means 8 on the one hand and the measurement surface on the other hand remains substantially constant.

Furthermore, the embodiment according to FIG. 1 comprises a travel measurement means which in the embodiment is formed by a rotational angle sensor 23 mounted to the wheel 21. The device of the invention further comprises a control device (not shown) for controlling the capture of the measurement signals of the radiation detector means 8 and an indicator means, also not shown, for outputting the measured values.

The embodiment of FIG. 1 is structured such that the radiation means or in this instance photo detector means 8 captures at least a portion of the light from the second radiation means 19 diffused by the measurement surface, i.e. non-collimated, and derive therefrom a parameter characteristic of the measurement surface by means of a not shown processor means.

Figure 2:
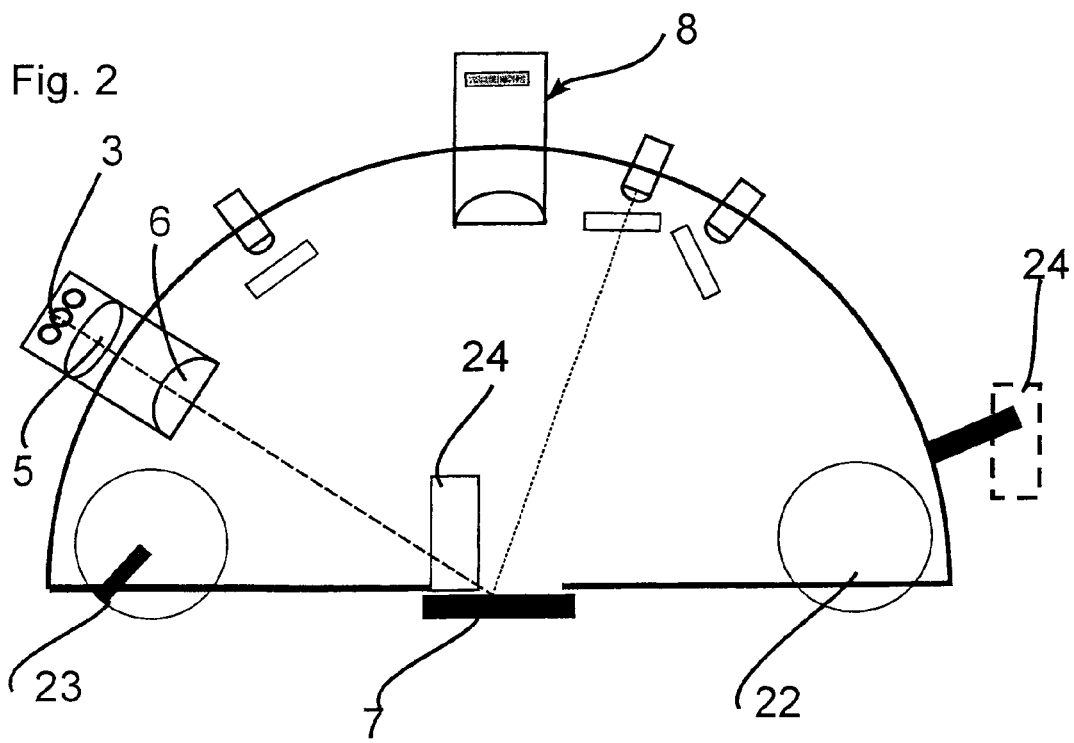
FIG. 2 another embodiment of the device of the present invention.

The embodiment of FIG. 2 furthermore comprises a coating-thickness measurement means 24 for determining the coating thickness of the measurement surface to be examined, whose coating-thickness sensor emits a measurement signal which is representative of the coating thickness to be determined.

Said coating-thickness measurement means may at least partially be positioned inside the housing or (illustrated in dashed lines) outside the housing. In a preferred embodiment the coating-thickness measurement means is a probe being in physical contact with the measurement surface. Unlike the embodiment of FIG. 1, the radiation detector means 8 is positioned perpendicular above the measurement surface 7.

Furthermore, in the embodiment of FIG. 2 there is provided a (not shown) processor means having a memory means which for example allows an allocation of the measurement signals from the radiation detector means and/or the coating-thickness measurement means in particular but not exclusively to the same location on the measurement surfaces.

The invention claimed is:

1. A device for measuring the properties of high-gloss or metallic finishes in particular of vehicle bodies, having:
   at least one first radiation means having at least one first radiation source which directs substantially collimated radiation at a predetermined angle towards a measurement surface;
   a plurality of second radiation means each having at least one second radiation source, each of which projects non-collimated radiation onto the measurement surface, wherein said plurality of second radiation means are spatially distributed to achieve a uniformly non-collimated radiation onto said measurement surface; and
   at least one radiation detector means which captures at least a portion of the radiation reflected and/or diffused off the measurement surface and emits at least one measurement signal which is characteristic of the reflected and/or diffused radiation,
   wherein said radiation detector means comprises a device for detecting incident radiation dependent on a wavelength of said radiation.

2. The device according to claim 1,
   wherein an angle formed by a first geometrical connecting axis extending from the at least one radiation detector means to a geometrical center of the measurement surface and a projection of said first geometrical connecting axis to the measurement surface is variable.

3. The device according to claim 1, wherein a distance from said first radiation means to the measurement surface is between 1 cm and 30 cm, preferred between 2 cm and 20 cm, particularly preferred between 2 cm and 7 cm.

4. The device according to claim 1, wherein each said second radiation means comprises at least one radiation diffusor means.

5. The device according to claim 4, wherein said at least one radiation diffusor means is selected from a group of radiation diffusor means comprising radiation diffusor disks, frosted glass disks and diffusor films.

6. The device according to claim 4, wherein a diffusor surface of each said radiation diffusor means is mounted at a specified diffusor surface angle relative to the measurement surface, said angle defined by a geometrical connecting axis extending from a longitudinal axis of each said second radiation means to a geometrical center of the measurement surface, said specified diffusor surface angle being between 0 degrees and 90 degrees, preferred between 30 degrees and 90 degrees, particularly preferred between 75 degrees and 90 degrees.

7. The device according to claim 6, wherein a spatial orientation and position of said diffusor surface of said radiation diffusor means is variable relative to said geometrical connecting axis from said second radiation means to said geometrical center of the measurement surface.

8. The device according to claim 1, wherein said at least one first radiation means and said plurality of second radiation means are positioned in a housing above the measurement surface.

9. The device according to claim 8, wherein a space inside the housing has substantially radiation-absorbing properties.

10. The device according to claim 8, wherein said housing is substantially configured radiation-proof, preferably light-proof, such that substantially no radiation can enter the housing other than such radiation as diffused and/or reflected off the measurement surface.

11. The device according to claim 1, wherein said second radiation means are positioned on a geometrical spherical surface or a geometrical surface of a rotational ellipsoid above the measurement surface.

12. The device according to claim 1, wherein at least one radiation source is variable in at least one radiation parameter selected from a group comprising radiation intensity, radiation wavelength, direction of radiation polarization, and temporal radiation intensity modulation.

13. The device according to claim 1, wherein at least two of said first and second radiation sources are variable independent of each other in at least one radiation parameter.

14. The device according to claim 1, wherein said first and second radiation sources are selected from a group of radiation sources comprising thermal radiation sources, in particular but not exclusively light bulbs, halogen light bulbs, coherent and non-coherent semiconductor radiation sources, gas discharge radiation sources and lasers.

15. The device according to claim 1, wherein at least two of said first and second radiation sources and/or radiation detector means have different spectral radiation characteristics.

16. The device according to claim 1, wherein the radiation from said first radiation means is collimated by at least one radiation directing means.

17. The device according to claim 16, wherein said at least one radiation directing means comprises at least one radiation directing component selected from a group of radiation directing components comprising lens components, micro lens components, micro lens arrays, diffracting components, reflector components, in particular but not exclusively parabolic reflectors, grating components, volume grating components and holographic components.

18. The device according to claim 1, wherein said first radiation means comprises at least one diaphragm means, preferably but not limited to apertured diaphragms positioned in a path of radiation.

19. The device according to claim 1, wherein said device is movable relative the measurement surface such that a distance between the first and second radiation means and the measurement surface remains substantially constant.

20. The device according to claim 1, wherein at least one travel measurement means is provided which emits at least one measurement signal corresponding to a traveled distance of the travel measurement means from the device to the measurement surface.

21. The device according to claim 20, further including a housing;
wherein said at least one travel measurement means is positioned inside and/or outside the housing.

22. The device according to claim 1, wherein at least one coating-thickness measurement means is provided for determining a coating thickness of the measurement surface to be examined comprising at least one coating thickness sensor which emits a measurement signal representative of the coating thickness to be determined.

23. The device according to claim 22, further including a housing;
wherein said at least one coating-thickness measurement means is positioned inside and/or outside the housing.

24. The device according to claim 1, further including a travel measurement means and a coating-thickness measurement means;
wherein at least one processor means and one memory means is provided which allow an allocation of the measurement signals of the radiation detector means and/or the measurement signals of the travel measurement means and/or the coating-thickness measurement means to specified locations, in particular but not exclusively to the same location on the measurement surfaces.

25. A method for measuring the properties of high-gloss or metallic finishes in particular of vehicle bodies, using a device according to claim 1,
wherein, said at least one first radiation means directs collimated radiation at a predetermined angle towards the measurement surface, and wherein
said plurality of second radiation means project at least a portion of the non-collimated radiation onto the measurement surface;
and wherein said at least one radiation detector means captures at least a portion of the radiation reflected and/or diffused off the measurement surface and emits at least one measurement signal which is characteristic for the incident radiation and which is dependent on a wavelength of said radiation;

and wherein at least one control means is provided which controls the capture of at least one measurement signal of the radiation detector means; and and wherein at least one output means is provided which outputs at least one measurement result.

26. The method according to claim 25, wherein at least one processor means is provided for evaluating the measurement signals and deriving therefrom at least one parameter which characterizes the properties of the measurement surface and which can be output at least on one output means.

27. The method according to claim 25, further including a travel measurement means and a coating-thickness measurement means;

wherein at least one control means is provided for controlling the capture of the measurement signals from the radiation detector means and/or the travel measurement means and/or the coating-thickness measurement means and stores same in at least one provided memory means.

28. The method according to claim 25, wherein the radiation from said second radiation means is substantially reflected and/or diffused only once off the measurement surface and/or off a surface substantially parallel thereto.

29. The device according to claim 1, wherein a space above the measurement surface has substantially radiation-absorbing properties.

30. The device according to claim 1, wherein an angle formed by a second geometrical connecting axis extending from the at least one first radiation means to the geometrical center of the measurement surface and a projection of said second connecting axis onto the measurement surface, is variable.

31. A device for measuring the properties of high-gloss or metallic finishes in particular of vehicle bodies, having:

a housing positioned above a measurement surface;

at least one first radiation means positioned in said housing and having at least one first radiation source which directs substantially collimated radiation at a predetermined angle towards the measurement surface;

a plurality of second radiation means positioned in said housing and having at least one second radiation source, each of which projects substantially non-collimated radiation onto the measurement surface, said plurality of second radiation means being equally distributed on a geometrical spherical surface or a geometrical surface of a rotational ellipsoid; and at least one radiation detector means which captures at least a portion of the radiation reflected and/or diffused off the measurement surface and emits at least one measurement signal which is characteristic of the reflected and/or diffused radiation, wherein said radiation detector means comprises a device for detecting incident radiation dependent on a wavelength of said radiation.

* * * * *